United States Patent
Yankov et al.

(10) Patent No.: US 6,177,456 B1
(45) Date of Patent: Jan. 23, 2001

(54) MONOHALOCEPHALOMANNINES HAVING ANTICANCER AND ANTILEUKEMIC ACTIVITY AND METHOD OF PREPARATION THEREFOR

(75) Inventors: Luben K. Yankov, Edison; Ramesh C. Pandey, Highland Park, both of NJ (US)

(73) Assignee: Xechem International, Inc., New Brunswick, NJ (US)

( * ) Notice: Under 35 U.S.C. 154(b), the term of this patent shall be extended for 0 days.

(21) Appl. No.: 09/113,462

(22) Filed: Jul. 10, 1998

Related U.S. Application Data

(63) Continuation-in-part of application No. 08/974,404, filed on Nov. 19, 1997, now abandoned, which is a continuation of application No. 08/936,710, filed on Sep. 24, 1997, now abandoned, which is a continuation-in-part of application No. 08/654,424, filed on May 29, 1996, now Pat. No. 5,807,888, which is a continuation-in-part of application No. 08/672,397, filed on May 29, 1996, now Pat. No. 5,854,278, which is a continuation-in-part of application No. 08/571,427, filed on Dec. 13, 1995, now Pat. No. 5,840,748, which is a continuation-in-part of application No. 08/572,240, filed on Dec. 13, 1995, now Pat. No. 5,654,448, which is a continuation-in-part of application No. 08/530,846, filed on Oct. 2, 1995, now abandoned.

(51) Int. Cl.⁷ ..................... A61K 31/337; C07D 305/14

(52) U.S. Cl. .................. 514/449; 549/510; 549/511
(58) Field of Search .................. 549/510, 511, 549/449

(56) References Cited

U.S. PATENT DOCUMENTS

| | | | |
|---|---|---|---|
| 4,814,470 | 3/1989 | Colin et al. | 514/449 |
| 4,924,011 | 5/1990 | Denis et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,019,504 | 5/1991 | Christen et al. | 435/123 |
| 5,059,699 | 10/1991 | Kingston et al. | 549/511 |
| 5,136,060 | 8/1992 | Holton | 549/510 |
| 5,157,049 | 10/1992 | Haugwitz et al. | 514/449 |
| 5,175,315 | 12/1992 | Holton | 549/510 |
| 5,194,635 | 3/1993 | Kingston et al. | 549/430 |
| 5,200,534 | 4/1993 | Rao | 549/510 |
| 5,202,448 | 4/1993 | Carver et al. | 549/510 |
| 5,227,400 | 7/1993 | Holton et al. | 514/444 |
| 5,229,526 | 7/1993 | Holton | 549/213 |
| 5,243,045 | 9/1993 | Holton et al. | 544/60 |
| 5,248,796 | 9/1993 | Chen et al. | 549/510 |
| 5,250,683 | 10/1993 | Holton et al. | 544/60 |
| 5,250,722 | 10/1993 | Bombardelli et al. | 560/104 |
| 5,254,580 | 10/1993 | Chen et al. | 514/449 |
| 5,254,703 | 10/1993 | Holton | 549/510 |
| 5,272,171 | 12/1993 | Ueda et al. | 514/449 |
| 5,274,124 | 12/1993 | Holton | 549/214 |
| 5,278,324 | 1/1994 | Kingston et al. | 549/510 |
| 5,279,949 | 1/1994 | Nair | 435/123 |
| 5,283,253 | 2/1994 | Holton et al. | 514/444 |
| 5,284,864 | 2/1994 | Holton et al. | 514/449 |
| 5,284,865 | 2/1994 | Holton et al. | 514/449 |
| 5,294,637 | 3/1994 | Chen et al. | 514/449 |
| 5,296,506 | 3/1994 | Kingston et al. | 514/449 |
| 5,300,638 | 4/1994 | Farina et al. | 540/357 |
| 5,310,672 | 5/1994 | Wann et al. | 435/240 |
| 5,319,112 | 6/1994 | Kingston et al. | 549/510 |
| 5,334,732 | 8/1994 | Murray et al. | 549/510 |
| 5,336,684 | 8/1994 | Murray et al. | 514/449 |
| 5,336,785 | 8/1994 | Holton | 549/214 |
| 5,338,872 | 8/1994 | Holton et al. | 549/510 |
| 5,412,092 | 5/1995 | Rey et al. | 540/200 |
| 5,470,866 | 11/1995 | Kingston et al. | 514/376 |
| 5,473,055 | 12/1995 | Mongelli et al. | 530/329 |
| 5,475,011 | 12/1995 | Ojima et al. | 514/320 |
| 5,475,120 | 12/1995 | Rao | 549/510 |

OTHER PUBLICATIONS

Powell, et al., "Cephaloannine; a New Antitumor Alkaloid from *Cephalotaxus mannii*", j.c.s. Chem. Comm., pp. 102–105 (1979).

Swindell et al., "Biologically Active Taxol Analogues with Depleted A–0Ring Side Chain Substitutents and Variable C–2' Configurations", *J. Med. Chem.* 34 (37:1176–1184 (1991)).

*Primary Examiner*—Ba K. Trinh
(74) *Attorney, Agent, or Firm*—Dorsey & Whitney LLP

(57) ABSTRACT

The present invention provides a 3"-monohalocephalomannine of the formula:

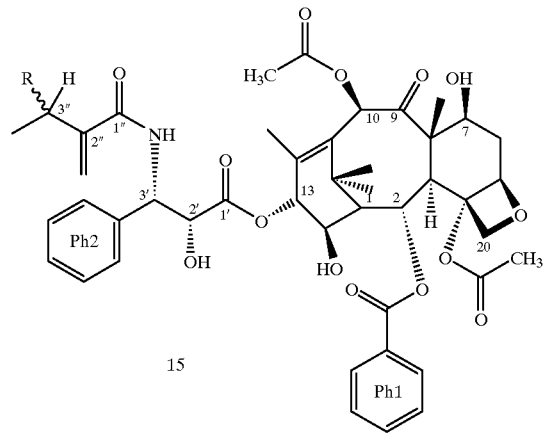

wherein R is halogen.

9 Claims, 9 Drawing Sheets

1. 10-deacetyl-7-epi-paclitaxel
2. paclitaxel (standard)
3. 3"-monochlorocephalomannine

MONOHALOCEPHALOMANNINES HAVING ANTICANCER AND ANTILEUKEMIC ACTIVITY AND METHOD OF PREPARATION THEREFOR

RELATED APPLICATIONS

This application is a continuation-in-part of U.S. application Ser. No. 08/974,404, filed Nov. 19, 1997, now abandoned which is a continuation of U.S. application Ser. No. 08/936,710, filed Sep. 24, 1997, now abandoned, which is a continuation-in-part of U.S. application Ser. No. 08/654,424, filed May 29, 1996, now U.S. Pat. No. 5,807,888, and U.S. application Ser. No. 08/672,397, filed May 29, 1996, now U.S. Pat. No. 5,854,278, which are both continuations-in-part of U.S. application Ser. No. 08/571,427, filed Dec. 13, 1995, now U.S. Pat. No. 5,840,748, which is a continuation-in-part of U.S. application Ser. No. 08/572,240, filed Dec. 13, 1995, now U.S. Pat. No. 5,654,448, which is continuation-in-part of U.S. application Ser. No. 08/530,846, filed Oct. 2, 1995, now abandoned.

FIELD OF THE INVENTION

The present invention is directed to novel monohalogenated cephalomannine derivatives, their preparation and methods of use as effective anticancer and antileukemic agents, and as alternatives to paclitaxel for use in bioactivity testing.

BACKGROUND OF THE INVENTION

Several important compounds from the taxane family of diterpenes have been identified as possessing strong antineoplastic activity against various cancers. For example, paclitaxel (1), having the following structure,

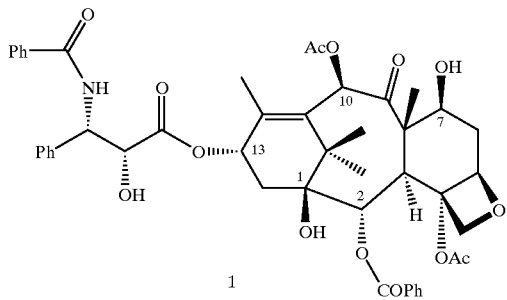

has been approved by the Food and Drug Administration for the treatment of ovarian and breast cancers and Karposi sarcoma, and is presently undergoing clinical trials for treatment of various other cancers, including lung and colon cancer.

Cephalomannine has been reported to be effective in causing remission of leukemic tumors (see U.S. Pat. No. 4,206,221) and is most often present with its structurally similar analog, paclitaxel. The structure of cephalomannine (2) is shown below:

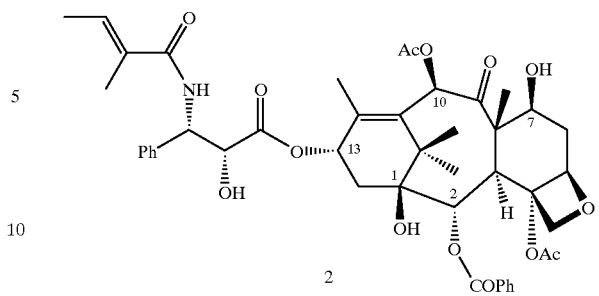

Paclitaxel and cephalomannine are only some of the many natural products from the taxane family which can be found, for example, in the bark of the Pacific yew tree Taxus brevifolia and other yew species such as T. baccata, T. cuspidata, as well as T. yvunnanensis and other plant materials including T. hicksii, T. densiforinis, T. gem, T. wardii, T. capitata, T. brownii, and T. dark green spreader. These compounds can also be found in Cephalotaxus species, such as, for example, Cephalotaxus manni as well as cultured plant cells and fungi.

The supply of paclitaxel, cephalomannine and other important taxanes is, however, limited to a finite amount of yew trees and other vegetation in which they are present in small amounts. Thus, alternative compounds having paclitaxel-like or cephalomannine-like anti-tumor and/or anti-leukemic activity are highly desirable to increase the armamentarium of clinical therapeutic agents.

In U.S. application Ser. No. 08/654,424, filed May 29, 1996, and U.S. application Ser. No. 08/672,397, filed May 29, 1996, now U.S. Pat. Nos. 5,807,888 and 5,854,278 respectively, the entirety of each being incorporated by reference herein, the synthesis, separation and anticancer activity of several dihalocephalomannine diasteromers is provided. In this study, two diastereomeric 2",3"-dibromocephalomannines and their two corresponding 7-epimers were obtained by treatment of extracts of Taxus yunnanensis with bromine solution, under mild conditions. Treatment of the same extract with chlorine solution yielded four diasteromeric 2",3"-chlorocephalomannines. The diasteromeric mixtures were separated into the individual components by preparative HPLC on $C_{18}$ reversed-phase silica gel. A more efficient analytical separation was obtained on a pentafluorophenyl bonded phase. The compounds were isolated and fully identified by classic and modern methods. Slight differences were observed in the NMR spectra of the 7-epimers when compared to their 7β-OH analogs. On the basis of a comparison of physicochemical data, the bromo compounds were identified as (2"R,3"S)-dibromo- 7-epicephalomannine (3), (2"S,3"R)-dibromo-7-epicephalomannine (4),(2"R,3"S)-dibromocephalomannine (5), (2"S,3"R)-dibromocephalomannine (6). The chloro compounds were identified as (2"R,3"R)-dichlorocephalomannine (7), (2"S,3"S)-dichlorocephalomannine (8), (2"S,3"S)-dichlorocephalomannine (9), and (2"S,3"R)-dichlorocephalomannine (10).

Cytotoxic activity was tested against the NCI 60 human tumor cell line panel in comparison with paclitaxel and results were obtained showing strong antineoplastic activity against several tumor lines, including, but not limited to, leukemia cell line HL-60 (TB); Non-Small Cell Cancer Line NCI-H522; Colon Cancer Cell Lines COO 205 and HT29; CNS Cancer Cell Lines SF-539 and SNB-75; Ovarian Cancer Cell Line OVCAR-3; Renal Cancer Cell Line RXF- 393; and Breast Cancer Cell Lines MCF7, MDA-MB-231/ATCC, HS 578, MDA-MB-435 and MDA-N.

The structures of some of these dihalogenated cephalomannines are set forth below:

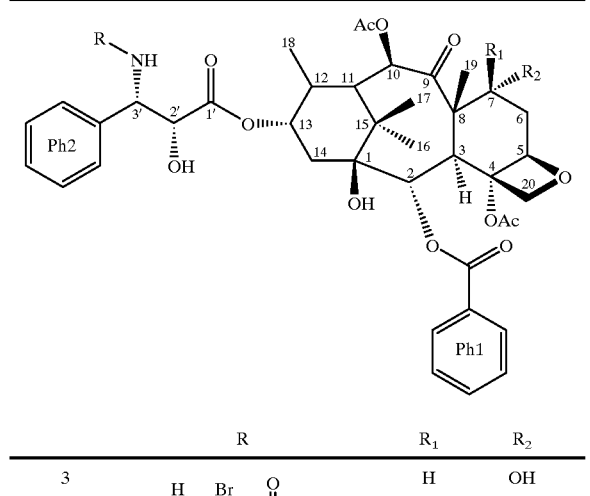

| | R | R₁ | R₂ |
|---|---|---|---|
| 3 | H,Br / Br (structure) | H | OH |
| 4 | Br,H / Br (structure) | H | OH |
| 5 | H,Br / Br (structure) | OH | H |
| 6 | Br,H / Br (structure) | OH | H |
| 7 | Cl,H / Cl (structure) | OH | H |
| 8 | H,Cl / Cl (structure) | OH | H |
| 9 | H,Cl / Cl (structure) | OH | H |

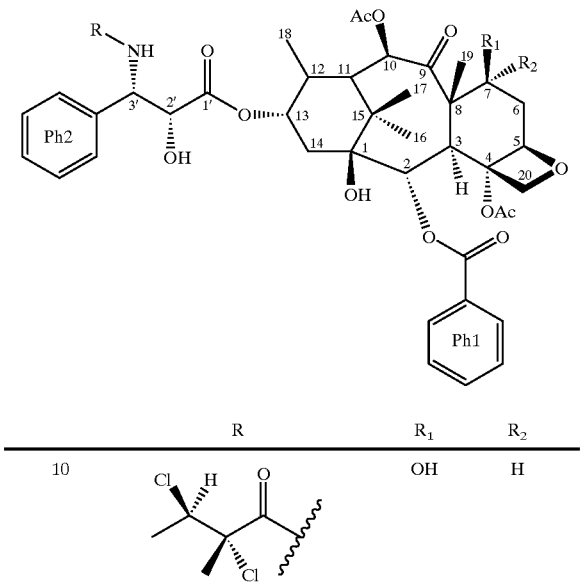

| | R | R₁ | R₂ |
|---|---|---|---|
| 10 | Cl,H / Cl (structure) | OH | H |

It would be highly desirable to provide additional new analogs of paclitaxel and cephalomannine having anti-neoplastic and/or anti-leukemic activity to add to the arsenal of bioactive and therapeutic compounds described above.

SUMMARY OF THE INVENTION

As discussed above, individual diastereomeric 2"3"-dichlorocephalomannine analogs have been isolated from extract of *Taxus yunnanensis* after chlorination of the extract. In accordance with the present invention, a more polar and more soluble monohalocephalomannine analog, 3"-monochlorocephalomannine, was discovered during separation and purification, which compound has the following structure:

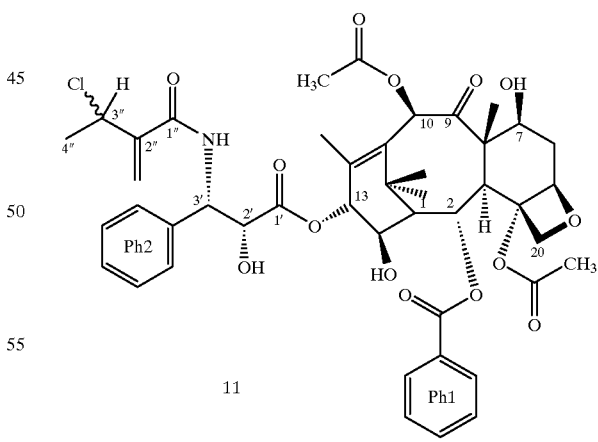

11

Cytotoxic activity testing of the inventive analog against the NCI 60 human cell line panel in comparison with paclitaxel demonstrates strong anti-neoplastic and anti-leukemic efficacy of the novel compound.

The invention is more fully discussed in the following detailed description with preferred embodiments with accompanying Figures.

DETAILED DESCRIPTION OF THE INVENTION WITH PREFERRED EMBODIMENTS

The present invention provides a novel compound of the, formula, (I)

[Structural formula of 3"-chlorocephalomannine]

which has been fully identified by classical and modern physicochemical methods as 13 -/N/-(E)-3"-chloro-2"-methylenebutenoyl-3'-phenyl-isosryl/oxy 2 -benzoyl-4 , 10β-diacetyloxy-1β, 7β-dihydroxy-5β, 20β-epoxy-tax-11-ene-9-One, or named shortly 3"-chlorocephalomannine (I).

Based on the structural differences between paclitaxel and cephalomannine, it has now been found that the side-chain double bond in cephalomannine can be selectively monohalogenated, and as shown in the exemplified specifically prepared embodiments, monochlorinated. In general terms, in illustrating the production of monochlorocephalomannine, the procedure can be conducted as follows.

EXAMPLE 1

To a dry fraction of an extract of *Taxus brevifolia* bark containing about 20% cephalomannine (as determined by HPLC), dissolved in 1,2-dichloroethane and cooled in a ice bath to about 0° C. is added dropwise a solution of chlorine in 1,2-dichloroethane, while stirring the mixture at the same temperature for approximately 3 hours. After the reaction is finished by checking for cephalomannine by following its disappearance in analytic $C_{18}$ reversed phase HPLC, the reaction is quenched with ice water. The 1,2-dichloroethane layer is washed by 1% sodium bisulfite and water to neutralize the reaction. After drying on sodium sulfate overnight and filtration, the solution is concentrated to a dry substance on a Buchi rotavapor under high vacuum.

The dry material, after several crystallizations, gives pure paclitaxel with chlorinated compounds remaining in the mother liquor. In addition to four dichlorocephalomannines, as discussed above, a more polar compound was also isolated.

Using running preparative HPLC of the combined mother liquors several times on a $C_{18}$ reversed phase column, a monochlorocephalomannine derivative was isolated.

After recrystallization with acetone/hexane (50:50) an amorphous white powder substance was obtained with M.P.=164–165° C.; UV(CH$_3$OH); λ max=221.3nm; (ε-18416.2); which proved to be 3"-monochlorocephalomannine of the present invention.

Figure 1:
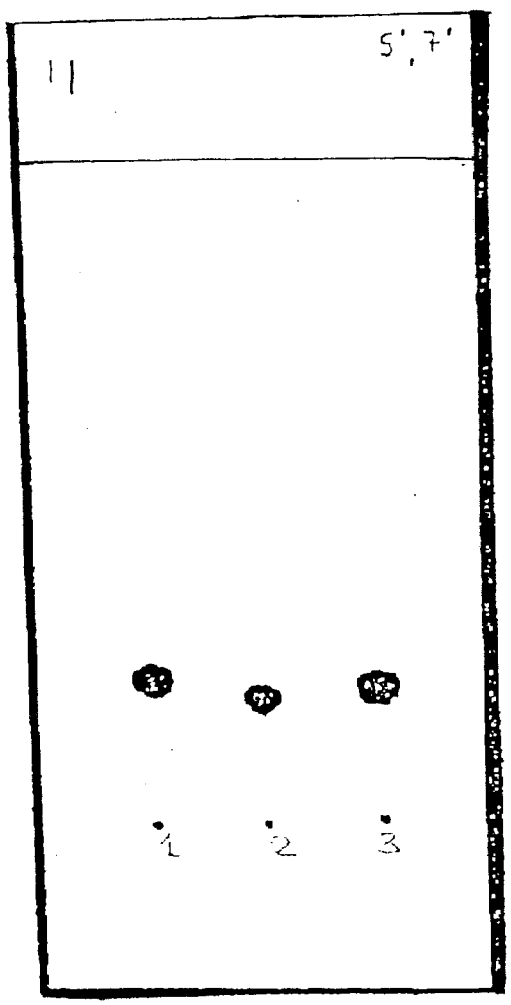
FIG. 1 illustrates a comparative TLC analysis of 3"-monochlorocephalomannine and paclitaxel.

FIG. 1 shows a comparison of TLC analysis of 3"-monochlorocephalomannine with pure paclitaxel, and with 3"-monochlorocephalomannine having $R_F$=0.21 and paclitaxel $R_F$=0.19.

Figure 2:
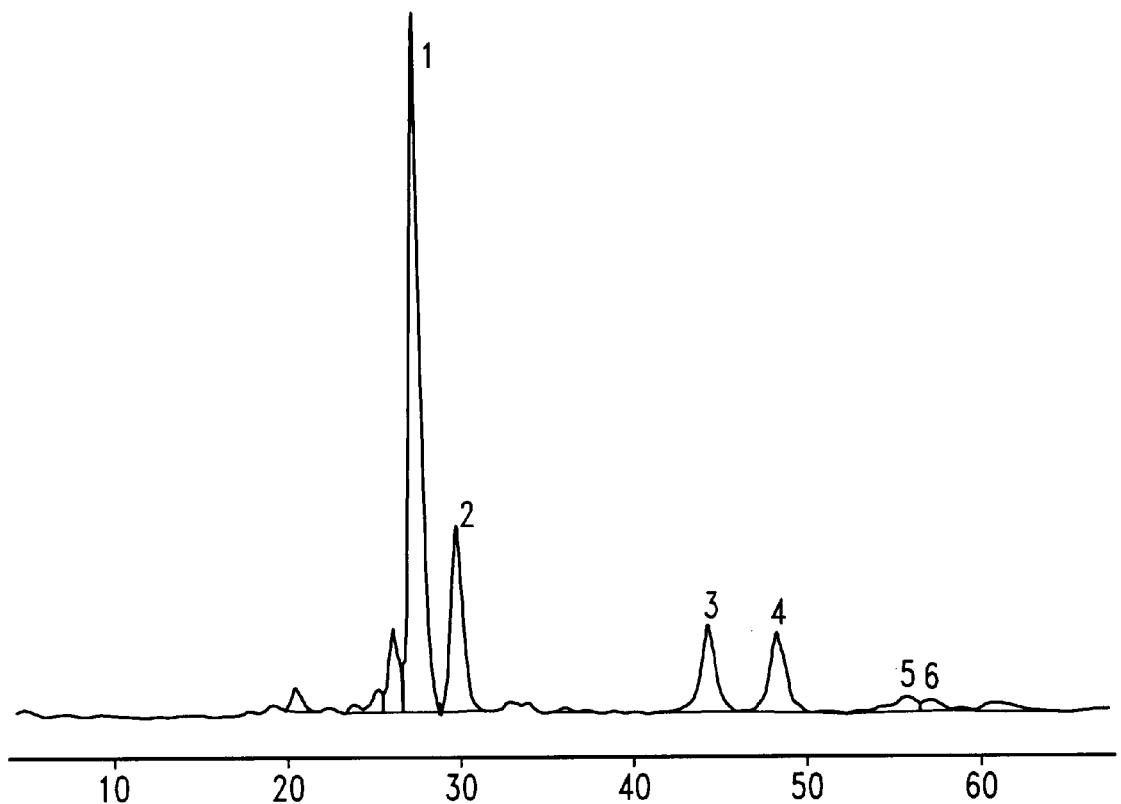
FIG. 2 is a HPLC chromatogram of 3"-monochlorocephalomannine, paclitaxel and dichlorocephalomannines.

TLC materials and conditions employed are as follows:
Silica gel 60 $F_{254}$ plate (Merck #5554)
Solvent system: hexane—CHCl$_3$-EtOAc-MeOH (20:60:15:5)
Spray reagent: 0.1% vanillin in 50:50 H$_2$SO$_4$-MeOH FIG. 2 is a HPLC chromatogram of a chlorinated extract of *Taxus yunnanensis* bark. This analysis was performed under the following conditions:
Column: ES Industries (FSP-H5); 5 μm; 60 Å; 4.6×250 mm
Solvent system: CH$_3$CN—MeOH—H$_2$O (39:20:41)
Flow rate: 0.5 ml/min., isocratic
Detector: Waters 990 photodiode array detector
Injection volume: 50 μl
Wavelength: 227 nm
Run time: 80 min.
The results are as follows:
Peak 1: paclitaxel
  RT$_1$=26.5 min.
Peak 2: 3"-monochlorocephalomannine
  RT$_2$=29.8 min.
Peaks 3–6: 2",3"-dichlorocephalomannines
  RT$_3$=44.7 min.
  RT$_4$=47.5 min.
  RT$_5$=56.2 min.
  RT$_6$=57.9 min.

Figure 3:
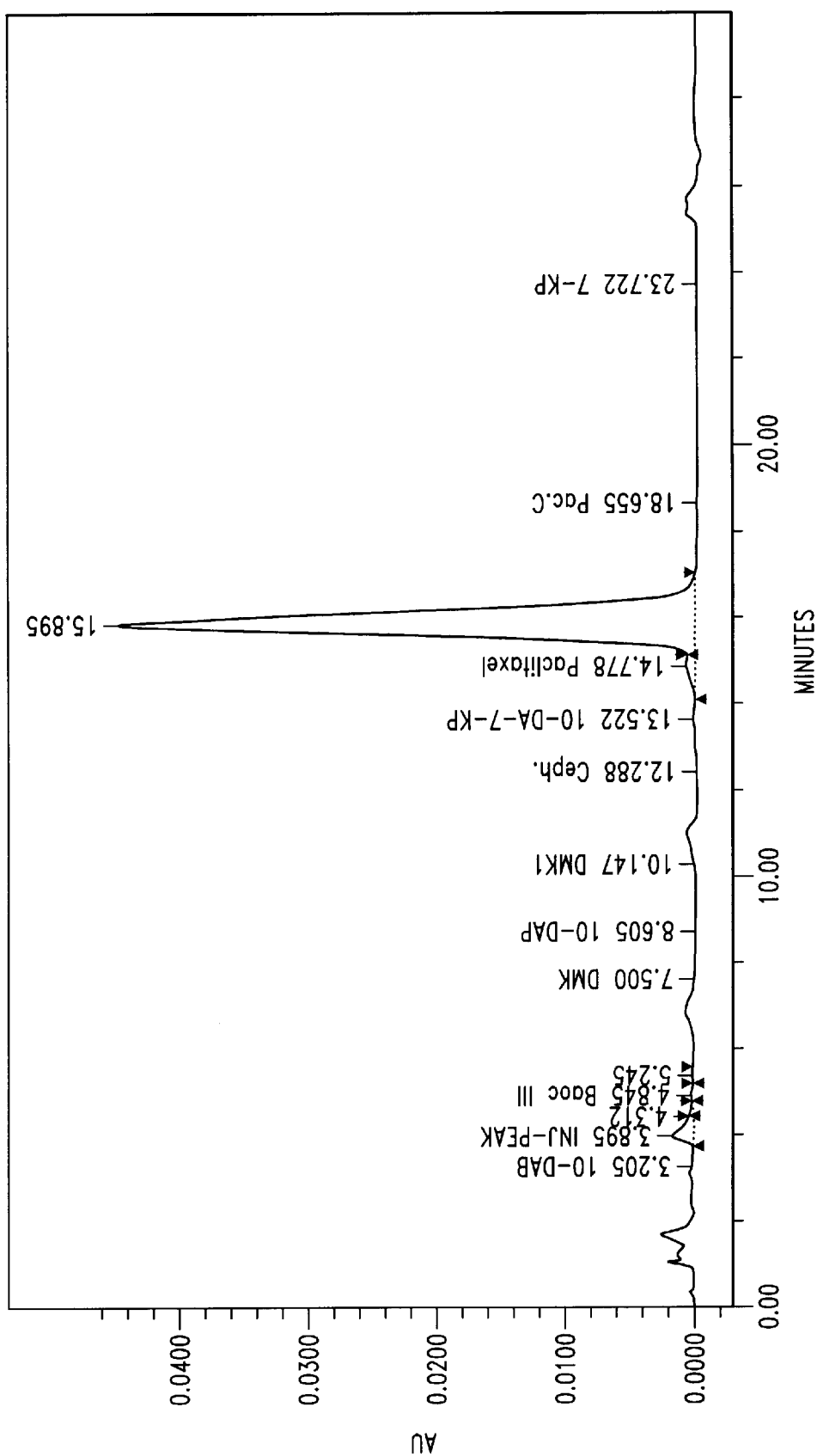
FIG. 3 are HPLC chromatograms of 3"-monochlorocephalomannine.

FIG. 3 is a HPLC chromatogram of 3"-chlorocephalomannine (Lot# XC-RN29-43-51) performed under the following conditions:
Column: ES Industries (FSP-H5); 5 μm; 60 Å, 4.6–250 mm
Solvent system: MeOH—CH$_3$CN—H$_2$O (20:35:45)
Flow rate: 1.5 ml/min., isocratic
Detector: Waters 990 photodiode array detector
Injection volume: 50 μl
Wavelength: 227 nm
Run time: 30 min.

Figure 4:
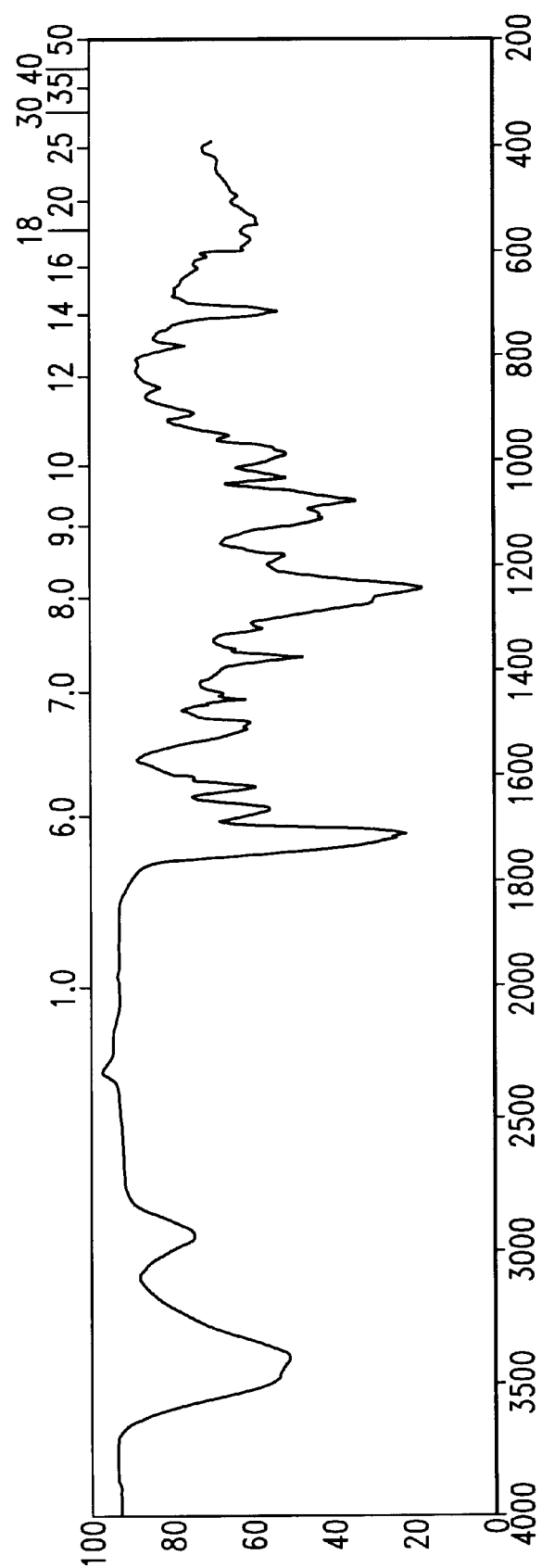
FIG. 4 is a IR spectrum of 3"-monochlorocephalomannine.

FIG. 4 is a IR spectrum of 3"-monochlorocephalomannine with the following analysis:

IR (KBr):(Bands are given in cm$^{-1}$).

As indicated, IR spectrum show bands for tertiary and secondary hydroxyl groups (3500, 1110, 1070 cm$^{-1}$), amide group acylated by aliphatic acid amine (3420, 1670, 1580 cm$^{-1}$), monosubstituted aromatic rings (3070, 1610, 1505, 770, 710 cm$^{-1}$), methyl, methylene and methene group in aliphatic or cyclic compounds, (2960, 2915, 2850, 1450, 1370 cm$^{-1}$), double bonds (3020, 1625, 1430, 1310, 980, 905 where 1425 and 905 cm$^{-1}$ show specific

type), esters of aromatic acids (1725, 1270 cm$^{-2}$), saturated cyclic six or larger membered carbonyl ring (1715, 1240 cm$^{-1}$),esters of acetic acid (1730, 1180 cm$^{-1}$), four membered oxetane ring (855 cm$^{-1}$), and monochlorinated chain (765 cm$^{-1}$).

Figure 5:
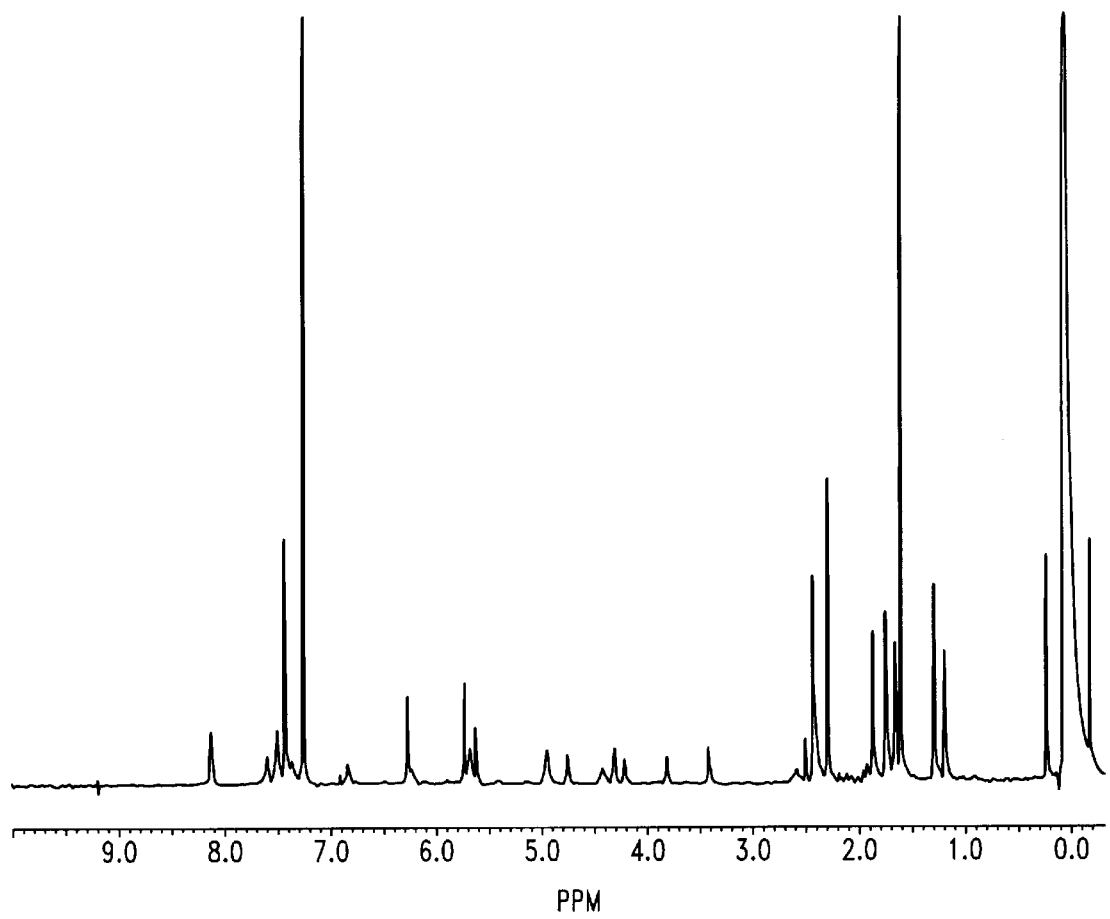
FIG. 5 is a $^1$H-NMR spectrum of 3"-monochlorocephalomannine.

FIG. 5 is a $^1$H-NMR spectrum of the inventive 3"-monochlorocephalomannine in CDCl$_3$ at 300 MHz, which is summarized below in Table 1.

TABLE 1

$^1$H-NMR (CDCl$_3$, BRUKER, 300 MHz)

| PROTONS | CHEMICAL SHIFT (PPM) | PROTONS | CHEMICAL SHIFT (PPM) |
|---|---|---|---|
| H-2 | 5.68(d,7.3) | H-3' | 5.69 (overlap) |
| H-3 | 3.80(d,7.2) | 2H-o-Ph1 | 8.13(dd,7.1,1.5) |
| H-5 | 4.95(d,8.1) | 2H-m-Ph1 | 7.50,(t,7.3) |
| H-6a | 2.55(m) | H-p-Ph1 | 7.61(5,7.3) |
| H-6b | 1.90(m) | 2H-o-Ph2 | 7.42(m) |
| H-7 | 4.41(m) | 2H-m-Ph2 | 7.42(m) |
| H-10 | 6.28 (S) | H-p-Ph2 | 7.37(m) |
| H-13 | 6.25(brs,8.9) | H-3" | 4.95(overlap) |
| H-14a | 2.31(m) | 3H-4" | 1.62(d,6.8) |
| H-14b | 2.31(m) | H-5"a | 5.73(s) |
| 3H-16 | 1.15(s) | H-5"b | 5.62(s) |
| 3H-17 | 1.26(s) | H-1 OH | 1.7(s) |
| 3H-18 | 1.82(s) | H-7 OH | 2.45(d,4.1) |
| 3H-19 | 1.69(s) | H-2'OH | 3.39(d,4.6) |
| H-20a | 4.31(ABd,8.5) | H-3'NH | 6.85(d,9.2) |
| H-20b | 4.21(ABd,8.1) | 3H-4-0Ac | 2.39(s) |
| H-2' | 4.73(d,2.5) | 3H-10-0Ac | 2.25(s) |

As shown in Table 1, there is depicted a spectrum which is typical for taxane structures with two singlets at 5.73 and 5.62 ppm for two protons from a >C=CH$_2$ group in the side chain.

Figure 6:
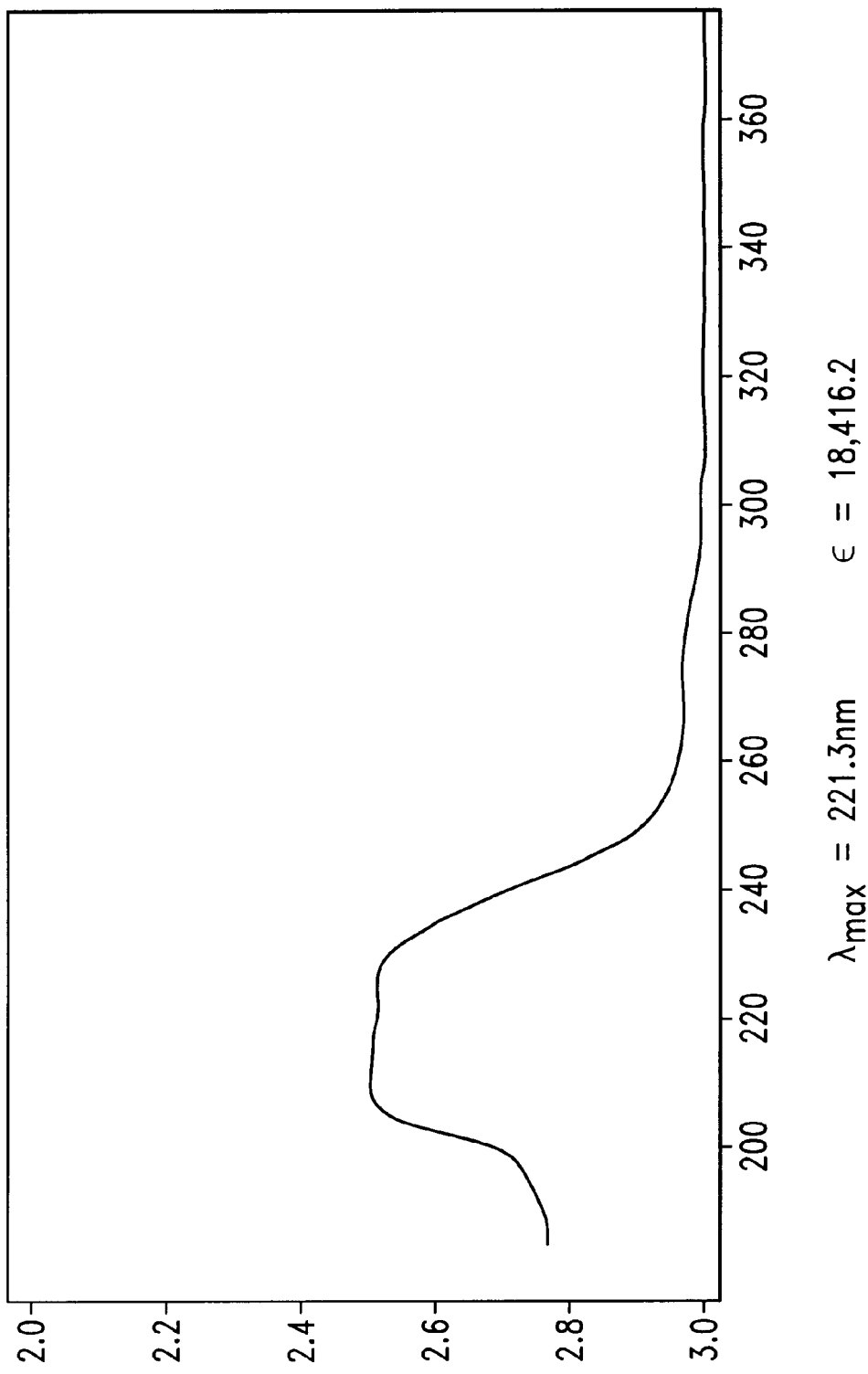
FIG. 6 is a UV spectrum of 3"-monochlorocephalomannine.

FIG. 6 is a UV spectrum of 3"-monochlorocephalomannine in MeOH, with, $\lambda_{max}$=221.3 nm $\epsilon$=13416.2

Figure 7:
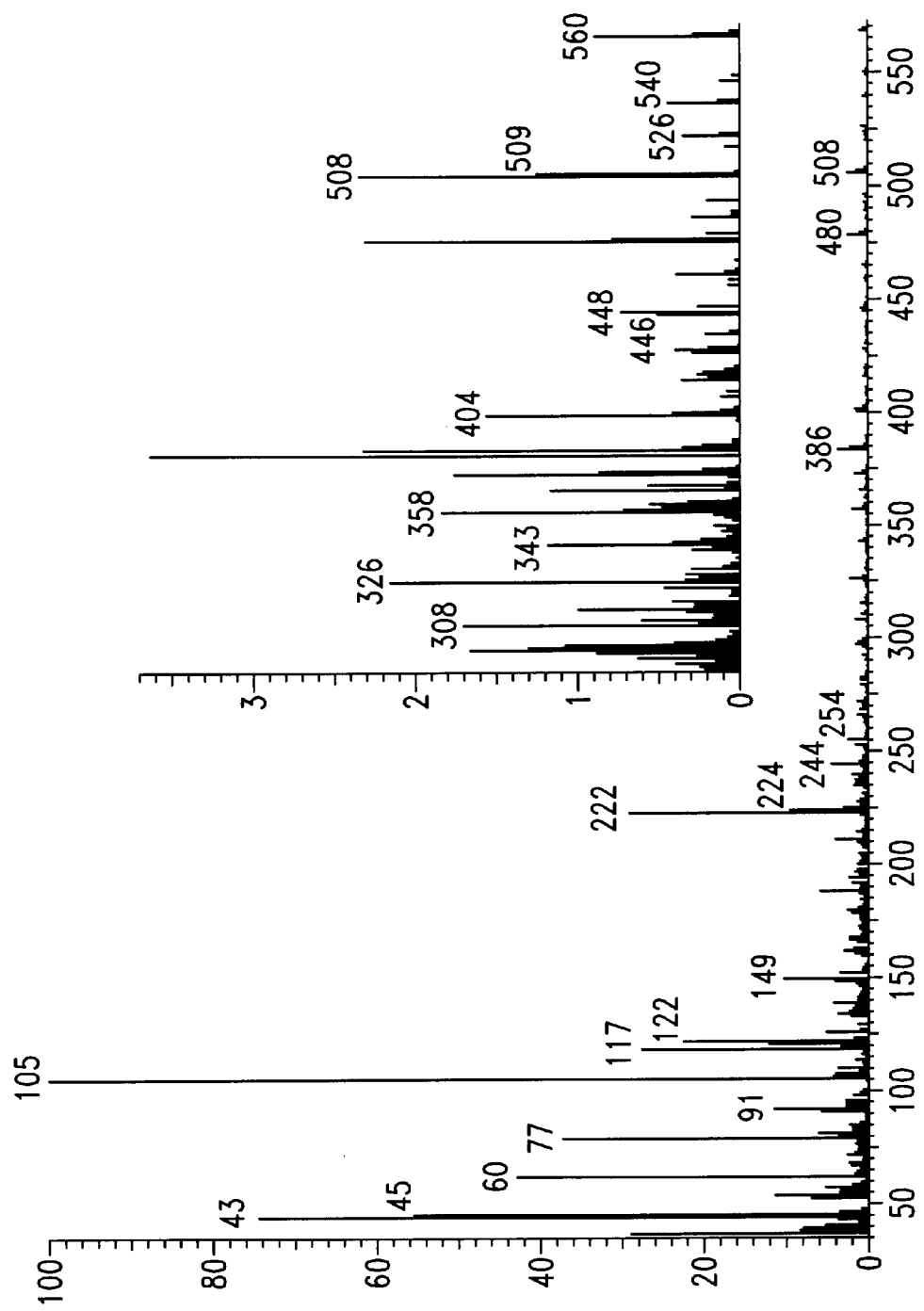
FIG. 7 is a EI-MS spectrum of 3"-monochlorocephalomannine.
Figure 8:
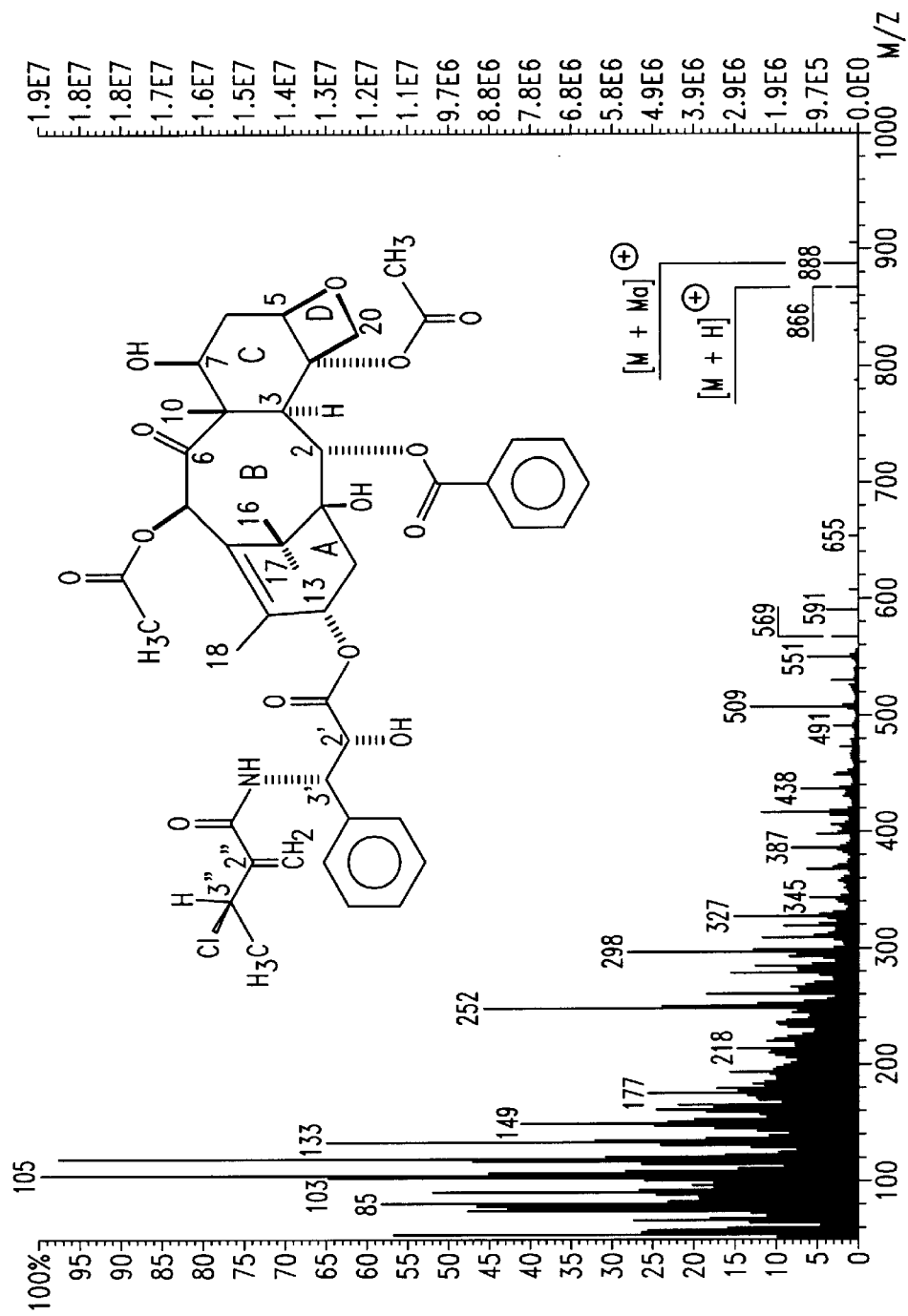
FIG. 8 is a FAB$^-$-MS spectrum of 3"-monochlorocephalomannine.
Figure 9:
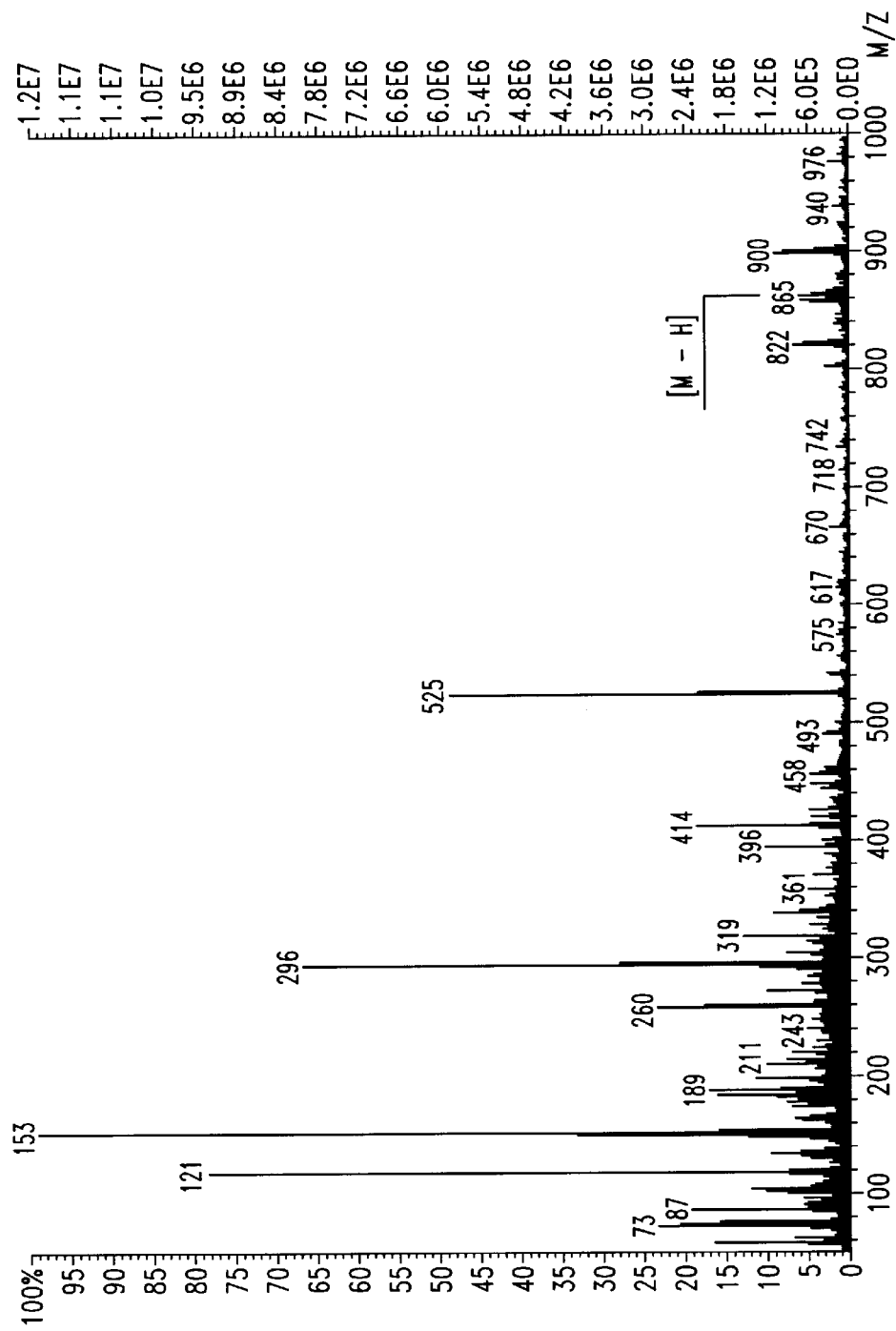
FIG. 9 is a FAB—MS spectrum of 3"-monochlorocephalomannine.

FIGS. 7, 8 and 9 show EIMS, FAB$^+$-MS and FAB$^-$—MS spectra of 3"-monochlorocephalomannine, the results of which are summarized below.

I-MS(FIG. 7): [M]$^+$865; m/z 568[T]$^+$;m/z 550 [T—H—H$_2$O]+; m/z 540; m/z 526 {T—Ac]$^+$;m/z 508[T—H—AcOH]$^+$; m/z 490[T—AcOH—H$_2$O]$^+$;m/z 480[T—AcOH—CO]$^+$; m/z 468[T—AcOH—Ac]$^+$; m/z 448 [T-2AcOH]$^+$; 446[T—BzOH]+; m/z 430[—2AcOH—H$_2$O]+; m/z 404 [T—BzOH—Ac]$^+$; m/z 386[T—BzOH—AcOH]+;m/z 368[T—BzOH—AcOH—H$_2$O]+; m/z 343 [T—BzOH—AcOH—Ac—2H]+;m/z 326 [T—BzOH—2AcOH]$^+$; m/z 308 [T—BzOH—2AcOH—H$_2$O]$^+$; m/z 298 [SH]$^+$; m/z 254 [SH—O—HCOH]$^+$m/z 222 [SH—O—CO—HCOH—2H]$^+$; m/z 149; m/z 122 [BzOH]$^+$; m/z 117 [C$_6$H$_6$ClCO]$^+$; m/z 105[Bz]$^+$; m/z 91[C$_7$H$_7$]+; m/z 77 [C$_6$H$_6$]+; m/z 60 [AcOH]$^+$m/z 43 [Ac];

The FAB$^+$-MS spectrum (FIG. 8) shows: [M+H]$^+$=866; [M+Na]$^+$=888;m/z 830[M—H$_2$O]$^+$;m/z 06[M—AcOH]$^+$; m/z 788[M—AcOH—H$_2$]$^+$; m/z 788[M—AcOH—2H$_2$O] m/z 762{MH—Bz+H]$^+$;m/z 750 [MH—C$_4$H$_6$ClCO+H]$^+$ m/z 744 [MH—BzOH]$^+$; m/z 708 [MH—BzOH—2H$_2$O]$^+$ m/z 691[M—BzOH—3H$_2$O]$^+$;m/z 685 [MH—BzOH—Ac—H$_2$O]$^+$;m/z 673[M—C$_4$H$_7$ClCON—AcOH]$^+$;m/z 666 [MH—BzOH—AcOH—H$_2$O]$^+$;m/z 655 [M—C$_4$H$_7$ClCON—AcOH—H$_2$O]$^+$;m/z 643[MH—Bz—AcOH]$^+$;m/z 626 [M—C$_7$H$_6$ClCO—BzOH]$^+$;m/z 609 [MH—C$_4$H$_6$ClCO—BzOH—H$_2$O]$^+$;m/z 591 [M—C$_4$H$_6$ClCO—AcOH—2H$^2$O]$^+$; m/z 569[T]$^+$; m/z 551 [T-H2O]$^+$; m/z 531 [T—2H$_2$O—2H]$^+$;m/z 509 [T—AcOH]$^+$;m/z 49 [T—AcOH—H$_2$O]$^+$;m/z 474[T—C$_6$H$_5$—H$_2$O]$^+$;m/z 449 [T—2AcOH]$^+$;m/z 447 [T—BzOH]$^+$; m/z 438 [T—C$_6$H$_5$—3H$_2$O]$^+$; m/z 416 [T—H—HCOH]$^+$;m/z 406 [T—BzOH—Ac]$^+$;m/z 387 [T—BzOH—AcOH]$^+$;m/z 370 [TH—BzOH—AcOH—H2O]$^+$;m/z 345 [T—BzOH—AcOH—Ac]$^+$;m/z 327 [T—BzOH—2AcOH]$^+$;m/z 309 [T—BzOH—2AcOH—H$^2$O]$^+$;m/z 298 [MH—T]$^+$;or [SH]$^+$;m/z 280[SH—H$_2$O]$^+$; m/z 264 [SH—O—H$_2$O]$^+$; m/z 252 [SH—CO—H$_2$O]$^+$;m/z 218 [SH—O—CO—2H$_2$O]$^+$;m/z 177 m/z 149; m/z 133 [C$_4$H$_6$ClCONH]$^+$;m/z 119/21 [BzOH]$^+$;m/z 105 [Bz]$^+$;m/z 91[C$_7$H$_7$]$^+$;m/z 85; m/z 77 [C$_6$H$_6$]$^+$;m/z 51[C$_4$H$_3$]$^+$m/z 43 [Ac]$^+$;

FIG. 9 is a FAB$^-$—MS spectrum of 3"-monochlorocephalomannine which shows [M-H]$^-$ at m/z 864 amu.

The elemental composition and molecular weight on the basis of R-FAB$^+$ were found as follows:

| | C$_{45}$H$_{53}$NO$_{14}$$^{35}$Cl [M + H]$^+$: |
|---|---|
| Calculated | 866.315459 |
| Found | 866.315500($\Delta$ m = 0.0 ppm). |
| | C$_{45}$H$_{53}$NO$_{14}$$^{37}$Cl [M + H]$^+$: |
| Calculated | 868.312509 |
| Found | 868.324300($\Delta$ m = -13.6 ppm). |
| | C$_{45}$H$_{52}$NO$_{14}$ClNa [M + Na]$^+$: |
| Calculated | 888.297403 |
| Found | 888.300900($\Delta$ m = -3.9 ppm) |
| | C$_{45}$H$_{52}$NO$_{14}$ClK [M + K]$^+$: |
| Calculated | 904.271342 |
| Found | 904.285300($\Delta$ m = 15.4 ppm). |

In accordance with the present invention, it is possible to halogenate, for example, chlorinate, the exocyclic side chain double bond on the taxane structure as shown in the above-described illustrative examples of a preferred embodiment, without other undesirable halogenation of the double bond in the taxane ring due to stearic hindrance, to provide through dehydrohalogenation of dihalocephalomannine a monohalo(chloro) derivative. It is thought that three isomers (A), (B) and (C) of unsaturated monochloro derivatives as shown below are possible.

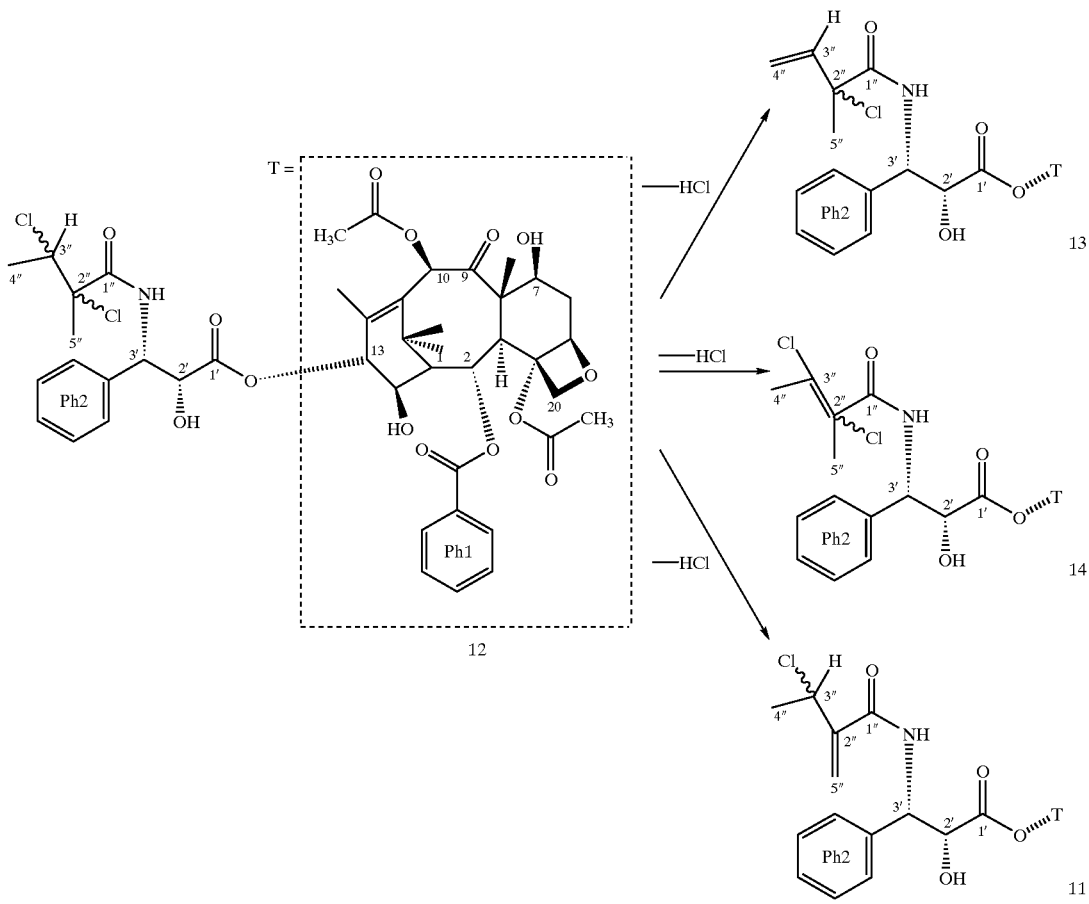

Without desiring to limit this invention to any particular theory, on the basis of information from classical and modern physicochemical methods for structural investigation of the natural organic compounds as shown above, it is thought that compound (C) in above shown equilibria answers the data most closely.

EXAMPLE 2

In Vitro Studies Showing Antitumor Efficacy of 3"-monochlorocephalomannine

The well-known anti-tumor drug paclitaxel shows highly desirable antitumor efficacy, and acts in a unique way by binding to microtubules to stabilize them from depolymerization, or inducing abnormal polymerization of tubuli, resulting in the disruption of cell mitosis and cancer cell proliferation. The mechanism of action of paclitaxel, pharmacology, etc., is described in detail, for example, in Rowinsky et al., "Taxol: A Novel Investigational Antimicrotubule Agent", 2 Natl. Cancer Inst., 82:1247 (1990).

In accordance with the present invention, the novel 3"-monohalocephalomannine compound show strong paclitaxel-like antitumor efficacy, which provides a valuable addition to the arsenal of antitumor therapeutic agents. The following in vitro studies conducted by the National Cancer Institute's Developmental Therapeutics Program demonstrate strong antitumor efficacy of the inventive monohalocephalomannines.

The Developmental Therapeutics Program provides as a service to the public an in vitro anticancer drug discovery screen using a panel of sixty different human tumor cell lines over which candidate drugs are tested at defined ranges of concentrations. See Boyd et al., Drug Development Research 34:90–109 (1995), the entirety of which is incorporated herein by reference.

As discussed in Boyd et al., the screen is designed and operated in such a manner that both relative and absolute sensitivities of each of the cell lines comprising the screen are reproducible to the degree that a characteristic profile ("fingerprint") of a respective cell line's response to a drug candidate can be generated.

Recent studies of the in vivo counterpart of the NCI in vitro screen have indicated the in vitro screen to be an effective selector of compounds with in vivo anticancer efficacy. See Grever et al., Proc. Am. Assoc. Cancer Res. 35:369 (1994).

Operation and interpretation of the screen are discussed in detail in Boyd et al., as well as in several other articles cited therein and thus need not be repeated here. In vitro efficacy of 3"-monochlorocephalomannine by dose response is shown in Tables 2 and 3, Testing Results and Mean Graphs, respectively.

TABLE 2

| | Time | | Mean Optical Densities | | | | | | Percent Growth | | | | | | |
|---|---|---|---|---|---|---|---|---|---|---|---|---|---|---|---|---|
| | | | | | Log10 Concentration | | | | | | | | | | |
| Panel/Cell Line | Zero | Ctrl | −8.3 | −7.3 | −6.3 | −5.3 | −4.3 | −8.3 | −7.3 | −6.3 | −5.3 | −4.3 | GI50 | TGI | LC50 |
| Leukemia | | | | | | | | | | | | | | | |
| CCRF-CEM | 0.279 | 1.202 | 1.168 | 1.171 | 0.895 | 0.941 | 0.758 | 96 | 97 | 67 | 72 | 52 | >5.00E − 05 | >5.00E − 05 | >5.00E − 05 |
| KL-60 (TB) | 0.242 | 1.008 | 0.973 | 0.533 | 0.478 | 0.462 | 0.629 | 95 | 38 | 31 | 29 | 51 | | >5.00E − 05 | >5.00E − 05 |
| K-562 | 0.141 | 1.261 | 1.094 | 1.089 | 0.538 | 0.437 | 0.463 | 85 | 85 | 35 | 26 | 29 | 2.53E − 07 | >5.00E − 05 | >5.00E − 05 |
| MOLT-4 | 0.567 | 2.023 | 1.997 | 2.326 | 1.327 | 0.868 | 0.661 | 98 | 121 | 52 | 21 | 6 | 5.88E − 07 | >5.00E − 05 | >5.00E − 05 |
| RPMI-8226 | 1.074 | 1.862 | 1.807 | 1.449 | 0.838 | 0.900 | 0.738 | 93 | 48 | −22 | −16 | −31 | 4.42E − 08 | 2.41E − 07 | >5.00E − 05 |
| SR | 0.468 | 1.657 | 1.518 | 0.920 | 0.656 | 0.523 | 0.421 | 88 | 38 | 16 | 5 | −10 | 2.89E − 08 | 1.03E − 05 | >5.00E − 05 |
| Non-Small Cell Lung Cancer | | | | | | | | | | | | | | | |
| A549/ATCC | 0.328 | 1.623 | 1.613 | 1.504 | 0.865 | 0.514 | 0.354 | 99 | 91 | 41 | 14 | 2 | 3.35E − 07 | >5.00E − 05 | >5.00E − 05 |
| EKVX | 0.315 | 0.732 | 0.677 | 0.658 | 0.542 | 0.422 | 0.396 | 87 | 82 | 54 | 26 | 19 | 7.10E − 07 | >5.00E − 05 | >5.00E − 05 |
| HOP-62 | 0.433 | 0.843 | 0.757 | 0.759 | 0.607 | 0.531 | 0.440 | 79 | 79 | 42 | 24 | 2 | 3.12E − 07 | >5.00E − 05 | >5.00E − 05 |
| HOP-92 | 0.312 | 1.008 | 0.873 | 0.881 | 0.624 | 0.607 | 0.394 | 81 | 82 | 45 | 42 | 12 | 3.62E − 07 | >5.00E − 05 | >5.00E = 05 |
| NCI-H226 | 0.476 | 1.001 | 0.884 | 0.822 | 0.555 | 0.540 | 0.518 | 78 | 66 | 15 | 12 | 8 | 1.02E − 07 | >5.00E − 05 | >5.00E − 05 |
| NCI-H23 | 0.546 | 1.544 | 1.555 | 1.399 | 0.728 | 0.609 | 0.409 | 101 | 85 | 18 | 6 | −25 | 1.68E − 07 | 7.94E − 06 | >5.00E − 05 |
| NCI-H322M | 0.405 | 1.384 | 1.370 | 1.326 | 0.700 | 0.569 | 0.395 | 99 | 94 | 30 | 17 | −2 | 2.44E − 07 | 3.72E − 05 | >5.00E − 05 |
| NCI-H522 | 0.224 | 0.454 | 0.464 | 0.409 | 0.214 | 0.114 | 0.135 | 105 | 80 | −5 | −49 | −40 | 1.14E − 07 | 4.40E − 07 | >5.00E − 05 |
| Colon Cancer | | | | | | | | | | | | | | | |
| COLO 205 | 0.329 | 1.210 | 1.239 | 1.109 | 0.403 | 0.247 | 0.090 | 103 | 88 | 8 | −25 | −73 | 1.51E − 07 | 8.96E − 07 | 1.67E − 05 |
| HCC-2998 | 0.137 | 0.627 | 0.611 | 0.375 | 0.132 | 0.051 | 0.002 | 97 | 49 | −4 | −63 | −98 | 4.66E − 08 | 4.19E − 07 | 3.00E − 06 |
| HCT-116 | 0.163 | 1.528 | 1.503 | 0.701 | 0.202 | 0.147 | 0.045 | 98 | 39 | 3 | −10 | −72 | 3.30E − 08 | 8.40E − 07 | 2.19E − 05 |
| HCT-15 | 0.210 | 1.533 | 1.493 | 1.529 | 1.305 | 0.446 | 0.156 | 97 | 100 | 83 | 18 | −26 | 1.60E − 06 | 1.28E − 05 | >5.00E − 05 |
| HT-29 | 0.132 | 0.881 | 0.797 | 0.420 | 0.141 | 0.096 | 0.038 | 89 | 38 | 1 | −28 | −71 | 2.95E − 08 | 5.48E − 07 | 1.63E − 06 |
| KM12 | 0.100 | 0.722 | 0.595 | 0.446 | 0.180 | 0.139 | 0.124 | 79 | 56 | 13 | 6 | 4 | 6.78E − 08 | >5.00E − 05 | >5.00E − 05 |
| SW-620 | 0.176 | 1.064 | 0.989 | 0.673 | 0.192 | 0.168 | 0.105 | 92 | 56 | 2 | −5 | −41 | 6.44E − 08 | 9.47E − 07 | >5.00E − 05 |
| CNS Cancer | | | | | | | | | | | | | | | |
| SF-268 | 0.373 | 1.084 | 1.011 | 0.951 | 0.600 | 0.420 | 0.299 | 90 | 81 | 32 | 7 | −20 | 2.15E − 07 | 8.85E − 06 | >5.00E − 05 |
| SF-295 | 0.415 | 1.290 | 1.263 | 1.208 | 0.716 | 0.185 | 0.144 | 97 | 91 | 34 | −55 | −65 | 2.63E − 07 | 1.21E − 06 | 4.36E − 06 |
| SF-539 | 0.491 | 1.440 | 1.324 | 1.214 | 0.639 | 0.223 | 0.169 | 88 | 76 | 16 | −55 | −66 | 1.35E − 07 | 8.43E − 07 | 4.30E − 06 |
| SNB-19 | 0.276 | 0.908 | 0.848 | 0.762 | 0.454 | 0.330 | 0.276 | 90 | 77 | 28 | 9 | 0 | 1.78E − 07 | >5.00E − 05 | >5.00E − 05 |
| SNB-75 | 0.443 | 0.820 | 0.739 | 0.727 | 0.590 | 0.306 | 0.298 | 78 | 75 | 39 | −31 | −33 | 2.47E − 07 | 1.80E − 06 | >5.00E − 05 |
| U251 | 0.293 | 1.169 | 1.135 | 0.976 | 0.515 | 0.269 | 0.202 | 96 | 78 | 25 | −8 | −31 | 1.70E − 07 | 2.85E − 06 | >5.00E − 05 |
| Melanoma | | | | | | | | | | | | | | | |
| LOX IMVI | 0.282 | 1.700 | 1.585 | 1.221 | 0.574 | 0.433 | 0.108 | 92 | 66 | 21 | 11 | −62 | 1.13E − 07 | 7.01E − 06 | 3.43E − 05 |
| MALME-3M | 0.445 | 0.783 | 0.793 | 0.645 | 0.508 | 0.454 | 0.313 | 103 | 59 | 18 | 3 | −30 | 8.40E − 08 | 5.98E − 06 | >5.00E − 05 |
| M14 | 0.276 | 1.072 | 1.039 | 0.942 | 0.419 | 0.202 | 0.069 | 96 | 84 | 18 | −27 | −75 | 1.63E − 07 | 1.26E − 06 | 1.51E − 05 |
| SK-MEL-2 | 1.225 | 1.848 | 1.800 | 1.691 | 1.614 | 1.255 | 0.572 | 92 | 75 | 63 | 5 | −53 | 8.25E − 07 | 6.07E − 06 | 4.39E − 05 |
| SK-MEL-5 | 0.135 | 1.002 | 1.055 | 0.541 | 0.234 | 0.320 | 0.016 | 106 | 47 | 11 | 21 | −88 | 4.43E − 08 | 7.83E − 06 | 2.24E − 05 |
| UACC-257 | 0.175 | 0.773 | 0.664 | 0.477 | 0.335 | 0.295 | 0.063 | 82 | 50 | 27 | 20 | −64 | 5.23E − 08 | 8.68E − 06 | 3.43E − 05 |
| UACC-62 | 0.473 | 1.691 | 1.662 | 1.296 | 0.820 | 0.787 | 0.201 | 98 | 68 | 28 | 26 | −58 | 1.41E − 07 | 1.02E − 05 | 4.06E − 05 |
| Ovarian Cancer | | | | | | | | | | | | | | | |
| IGRCV1 | 0.410 | 1.309 | 1.245 | 0.965 | 0.644 | 0.500 | 0.394 | 93 | 62 | 26 | 10 | −4 | 1.07E − 07 | 2.62E − 05 | >5.00E − 05 |
| OVCAR-3 | 0.529 | 1.393 | 1.208 | 1.117 | 0.459 | 0.445 | 0.268 | 78 | 68 | −13 | −16 | −49 | 8.33E − 08 | 3.44E − 07 | >5.00E − 05 |
| OVCAR-4 | 0.404 | 1.650 | 1.637 | 1.608 | 1.320 | 1.146 | 0.856 | 99 | 96 | 68 | 52 | 24 | 5.83E − 06 | >5.00E − 05 | >5.00E − 05 |
| OVCAR-5 | 0.612 | 0.971 | 0.939 | 0.934 | 0.702 | 0.587 | 0.258 | 91 | 90 | 25 | −4 | −58 | 2.06E − 07 | 3.62E − 06 | 3.57E − 05 |
| OVCAR-8 | 1.032 | 1.747 | 1.738 | 1.727 | 1.447 | 0.734 | 0.698 | 99 | 97 | 58 | −29 | −32 | 6.19E − 07 | 2.33E − 06 | >5.00E − 05 |
| SK-CV-3 | 0.689 | 1.198 | 1.145 | 1.128 | 0.769 | 0.562 | 0.555 | 90 | 86 | 16 | −18 | −20 | 1.63E − 07 | 1.44E − 06 | >5.00E − 05 |
| Renal Cancer | | | | | | | | | | | | | | | |
| 786-0 | 0.185 | 0.955 | 0.909 | 0.900 | 0.475 | 0.182 | 0.100 | 94 | 93 | 38 | −2 | −46 | 2.98E − 07 | 4.48E − 06 | >5.00E − 05 |
| ACHN | 0.130 | 0.638 | 0.554 | 0.523 | 0.324 | 0.308 | 0.155 | 83 | 77 | 38 | 35 | 5 | 2.50E − 07 | >5.00E − 05 | >5.00E − 05 |
| CAKI-1 | 0.372 | 1.053 | 1.038 | 1.125 | 0.921 | 0.758 | 0.481 | 98 | 111 | 80 | 57 | 16 | 7.26E − 06 | >5.00E − 05 | >5.00E − 05 |
| SN12C | 0.236 | 0.755 | 0.728 | 0.736 | 0.395 | 0.407 | 0.272 | 95 | 96 | 31 | 33 | 7 | 2.53E − 07 | >5.00E − 05 | >5.00E − 05 |
| TK-10 | 0.145 | 0.654 | 0.585 | 0.558 | 0.397 | 0.313 | 0.188 | 86 | 81 | 49 | 33 | 8 | 4.80E − 07 | >5.00E − 05 | >5.00E − 05 |
| UO-31 | 1.296 | 2.021 | 2.018 | 2.067 | 1.999 | 1.265 | 0.829 | 100 | 106 | 97 | −2 | −36 | 1.49E − 06 | 4.73E − 06 | >5.00E − 05 |
| Prostate Cancer | | | | | | | | | | | | | | | |
| PC-3 | 0.531 | 1.953 | 1.852 | 1.360 | 0.830 | 0.511 | 0.467 | 93 | 94 | 21 | −4 | −12 | 1.99E − 07 | 3.50E − 06 | >5.00E − 05 |
| DU-145 | 0.366 | 1.046 | 1.067 | 1.028 | 0.557 | 0.310 | 0.248 | 103 | 97 | 28 | −15 | −32 | 2.41E − 07 | 2.22E − 06 | >5.00E − 05 |
| Breast Cancer | | | | | | | | | | | | | | | |
| MCF7 | 0.232 | 1.214 | 1.149 | 0.768 | 0.345 | 0.327 | 0.202 | 93 | 55 | 11 | 10 | −13 | 6.39E − 08 | 1.34E − 05 | >5.00E − 05 |
| MCF7/ADR-RES | 0.757 | 1.202 | 1.167 | 1.217 | 1.062 | 0.717 | 0.263 | 92 | 103 | 69 | −5 | −65 | 8.95E − 07 | 4.24E − 06 | 2.78E − 05 |
| MDA-MB-231/ATCC | 0.380 | 0.774 | 0.779 | 0.726 | 0.580 | 0.497 | 0.244 | 101 | 88 | 51 | 30 | −36 | 5.43E − 07 | 1.42E − 05 | >5.00E − 05 |
| HS 578T | 0.346 | 0.756 | 0.637 | 0.616 | 0.382 | 0.268 | 0.226 | 71 | 66 | 9 | −23 | −35 | 9.45E − 08 | 9.47E − 07 | >5.00E − 05 |
| MDA-MB-435 | 0.321 | 1.366 | 1.151 | 0.361 | 0.096 | 0.108 | 0.155 | 79 | 4 | −70 | −67 | −52 | 1.23E − 08 | 5.64E − 08 | 2.68E − 07 |

TABLE 2-continued

| | Time | | Mean Optical Densities | | | | | Percent Growth | | | | | | | |
|---|---|---|---|---|---|---|---|---|---|---|---|---|---|---|---|
| | | | | | Log10 Concentration | | | | | | | | | | |
| Panel/Cell Line | Zero | Ctrl | −8.3 | −7.3 | −6.3 | −5.3 | −4.3 | −8.3 | −7.3 | −6.3 | −5.3 | −4.3 | GI50 | TGI | LC50 |
| MDA-N | 0.254 | 1.152 | 1.066 | 0.299 | 0.050 | 0.070 | 0.086 | 90 | 5 | −90 | −72 | −66 | 1.49E − 08 | 5.72E − 08 | 2.21E − 07 |
| BT-549 | 0.373 | 0.981 | 0.907 | 0.812 | 0.607 | 0.439 | 0.325 | 88 | 72 | 38 | 11 | −13 | 2.27E − 07 | 1.42E − 05 | >5.00E − 05 |
| T-470 | 0.525 | 1.295 | 1.311 | 1.207 | 0.858 | 0.833 | 0.722 | 102 | 89 | 43 | 40 | 26 | 3.55E − 07 | >5.00E − 05 | >5.00E − 05 |

TABLE 3

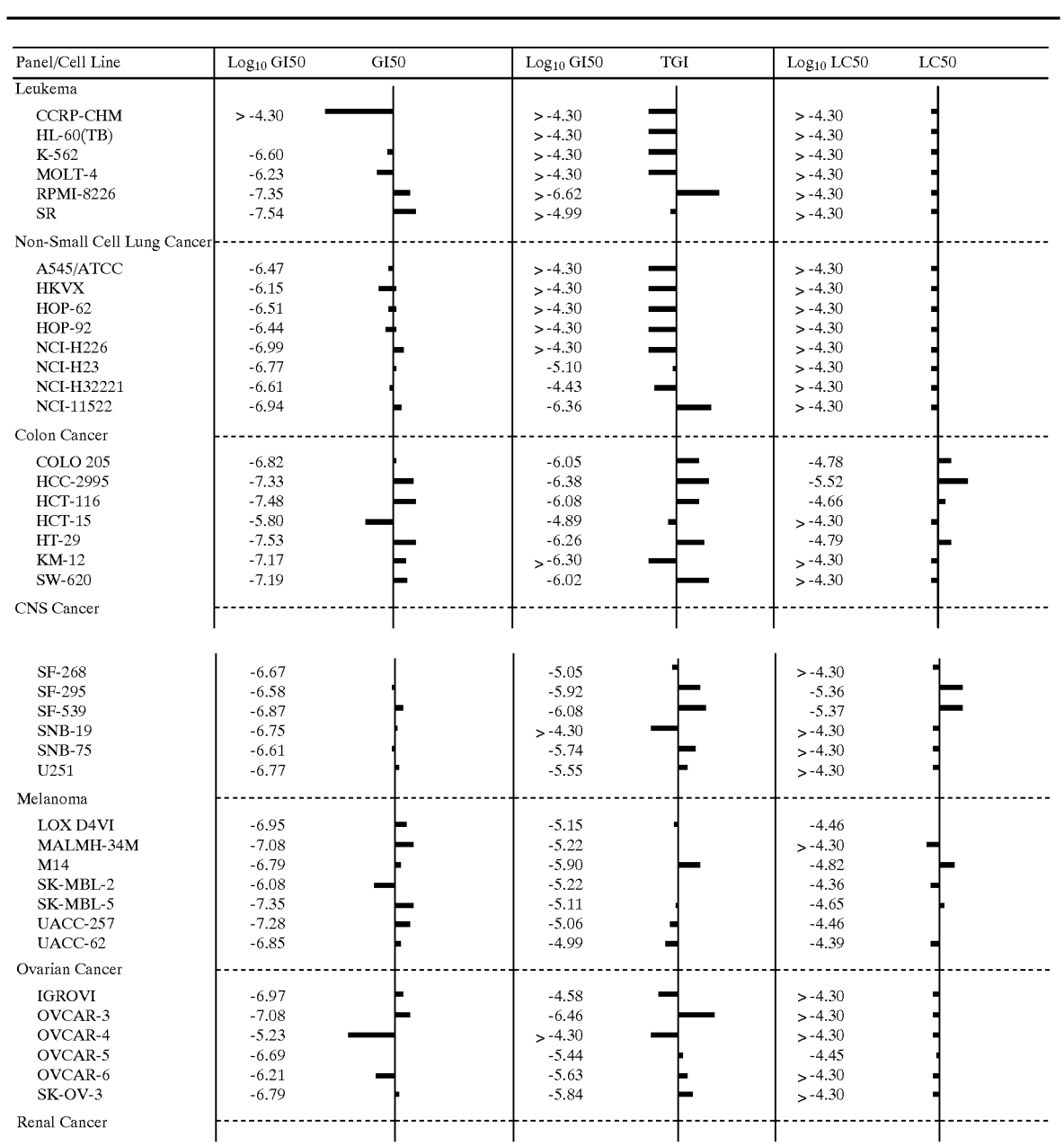

| Panel/Cell Line | Log₁₀ GI50 | GI50 | Log₁₀ GI50 | TGI | Log₁₀ LC50 | LC50 |
|---|---|---|---|---|---|---|
| Leukema | | | | | | |
| CCRP-CHM | > −4.30 | | > −4.30 | | > −4.30 | |
| HL-60(TB) | | | > −4.30 | | > −4.30 | |
| K-562 | −6.60 | | > −4.30 | | > −4.30 | |
| MOLT-4 | −6.23 | | > −4.30 | | > −4.30 | |
| RPMI-8226 | −7.35 | | > −6.62 | | > −4.30 | |
| SR | −7.54 | | > −4.99 | | > −4.30 | |
| Non-Small Cell Lung Cancer | | | | | | |
| A545/ATCC | −6.47 | | > −4.30 | | > −4.30 | |
| HKVX | −6.15 | | > −4.30 | | > −4.30 | |
| HOP-62 | −6.51 | | > −4.30 | | > −4.30 | |
| HOP-92 | −6.44 | | > −4.30 | | > −4.30 | |
| NCI-H226 | −6.99 | | > −4.30 | | > −4.30 | |
| NCI-H23 | −6.77 | | −5.10 | | > −4.30 | |
| NCI-H32221 | −6.61 | | −4.43 | | > −4.30 | |
| NCI-11522 | −6.94 | | −6.36 | | > −4.30 | |
| Colon Cancer | | | | | | |
| COLO 205 | −6.82 | | −6.05 | | −4.78 | |
| HCC-2995 | −7.33 | | −6.38 | | −5.52 | |
| HCT-116 | −7.48 | | −6.08 | | −4.66 | |
| HCT-15 | −5.80 | | −4.89 | | > −4.30 | |
| HT-29 | −7.53 | | −6.26 | | −4.79 | |
| KM-12 | −7.17 | | > −6.30 | | > −4.30 | |
| SW-620 | −7.19 | | −6.02 | | > −4.30 | |
| CNS Cancer | | | | | | |
| SF-268 | −6.67 | | −5.05 | | > −4.30 | |
| SF-295 | −6.58 | | −5.92 | | −5.36 | |
| SF-539 | −6.87 | | −6.08 | | −5.37 | |
| SNB-19 | −6.75 | | > −4.30 | | > −4.30 | |
| SNB-75 | −6.61 | | −5.74 | | > −4.30 | |
| U251 | −6.77 | | −5.55 | | > −4.30 | |
| Melanoma | | | | | | |
| LOX D4VI | −6.95 | | −5.15 | | −4.46 | |
| MALMH-34M | −7.08 | | −5.22 | | > −4.30 | |
| M14 | −6.79 | | −5.90 | | −4.82 | |
| SK-MBL-2 | −6.08 | | −5.22 | | −4.36 | |
| SK-MBL-5 | −7.35 | | −5.11 | | −4.65 | |
| UACC-257 | −7.28 | | −5.06 | | −4.46 | |
| UACC-62 | −6.85 | | −4.99 | | −4.39 | |
| Ovarian Cancer | | | | | | |
| IGROVI | −6.97 | | −4.58 | | > −4.30 | |
| OVCAR-3 | −7.08 | | −6.46 | | > −4.30 | |
| OVCAR-4 | −5.23 | | > −4.30 | | > −4.30 | |
| OVCAR-5 | −6.69 | | −5.44 | | −4.45 | |
| OVCAR-6 | −6.21 | | −5.63 | | > −4.30 | |
| SK-OV-3 | −6.79 | | −5.84 | | > −4.30 | |
| Renal Cancer | | | | | | |

TABLE 3-continued

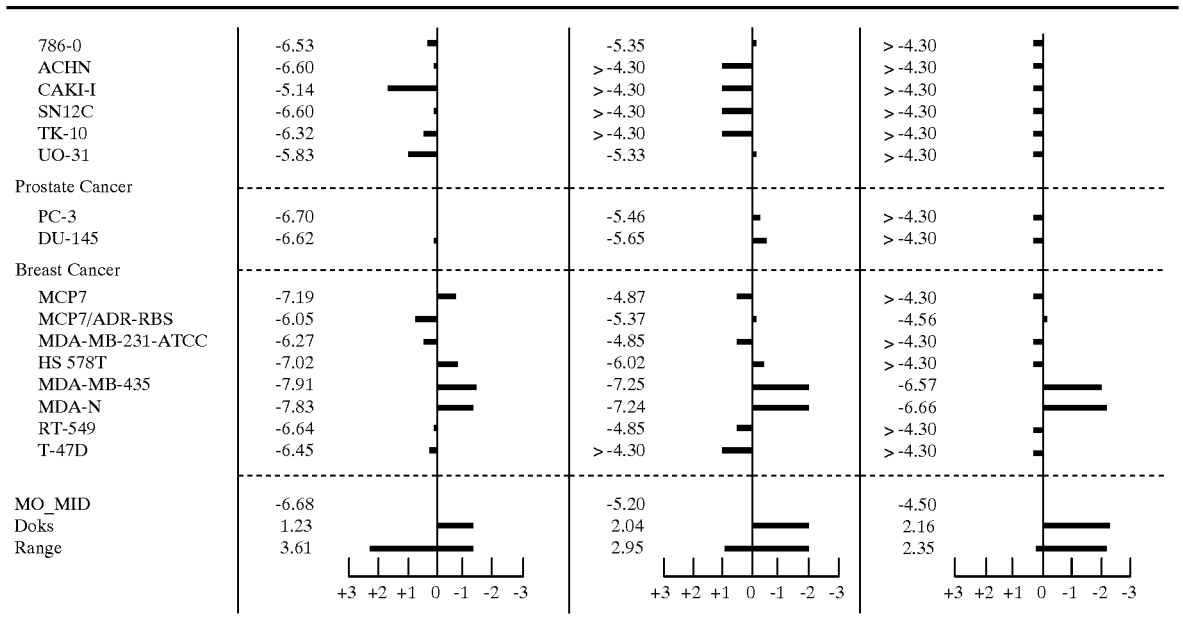

| | | | | | | |
|---|---|---|---|---|---|---|
| 786-0 | -6.53 | | -5.35 | | >-4.30 | |
| ACHN | -6.60 | | >-4.30 | | >-4.30 | |
| CAKI-I | -5.14 | | >-4.30 | | >-4.30 | |
| SN12C | -6.60 | | >-4.30 | | >-4.30 | |
| TK-10 | -6.32 | | >-4.30 | | >-4.30 | |
| UO-31 | -5.83 | | -5.33 | | >-4.30 | |
| Prostate Cancer | | | | | | |
| PC-3 | -6.70 | | -5.46 | | >-4.30 | |
| DU-145 | -6.62 | | -5.65 | | >-4.30 | |
| Breast Cancer | | | | | | |
| MCP7 | -7.19 | | -4.87 | | >-4.30 | |
| MCP7/ADR-RBS | -6.05 | | -5.37 | | -4.56 | |
| MDA-MB-231-ATCC | -6.27 | | -4.85 | | >-4.30 | |
| HS 578T | -7.02 | | -6.02 | | >-4.30 | |
| MDA-MB-435 | -7.91 | | -7.25 | | -6.57 | |
| MDA-N | -7.83 | | -7.24 | | -6.66 | |
| RT-549 | -6.64 | | -4.85 | | >-4.30 | |
| T-47D | -6.45 | | >-4.30 | | >-4.30 | |
| MO_MID | -6.68 | | -5.20 | | -4.50 | |
| Doks | 1.23 | | 2.04 | | 2.16 | |
| Range | 3.61 | | 2.95 | | 2.35 | |

Discussion of In Vitro Testing Results

As mentioned above in the NCI in vitro anticancer drug screen, the effect of an antitumor candidate, i.e., 3"-monochlorocephalomannine of the present invention, on a cell line, percentage growth (PG), and calculated response parameters are discussed in Boyd et al., "Data display and analysis strategies for the NCI-disease-oriented in vitro antitumor drug screen, *Cytotoxic Anticancer Drugs: Models and Concepts for Drug Discovery and Development*, Kluwer Academic Publishers, Amsterdam, pp. 11–34 (1992), and Monks et al., "Feasibility of a high-flux anticancer drug screen utilizing a diverse panel of human tumor cell lines in culture", *J. Natl. Cancer Inst.* 83:757–766 (1991), the entire disclosures of which are incorporated herein by reference. In general, in the screening data report, Table 2 and mean graphs, Table 3 "$GI_{50}$" represents the 50% growth inhibition factor, "TGI" represents a total growth inhibition, or cytostatic level of effect, and "$LC_{50}$" represents a lethal concentration, or net cell killing or cytotoxicity parameter. Values accompanied by a "<" signify that the dosage level or real value is a value that is something less than the lowest tested concentration, and values accompanied by a ">" indicate that the effective dosage or real value is a level greater than the highest tested concentration.

The mean graph of Table 3 is obtained from $GI_{50}$, TGI and $LC_{50}$ concentrations obtained for compounds tested against each cell line in the NCI in vitro screen. A detailed discussion of mean graph construction is also provided in Boyd et al. (1995). In interpreting the mean graphs in general, a bar projecting to the right represents sensitivity of a particular cell line to an anticancer/antileukemic candidate in excess of the average sensitivity of all tested cell lines, while bars extending to the left represent cell lines which are less sensitive on average to the anticancer/antileukemic candidate. As the bar scales are logarithmic, a bar which extends, for example, 2 or 3 units to the right of the vertical reference line in, say a $GI_{50}$ mean graph, indicates that the candidate drug compound achieved a response parameter for a particular cell line at a concentration one-hundredth to one-thousandth of the mean concentration required over all cell lines, therefore indicating that the particular tumor cell line is unusually sensitive to the tested candidate.

As shown by the instant results, the high magnitude of effect of monochlorocephalomannine on several cell lines in which the inventive compounds demonstrate a high response level include, for example, leukemia, non-small cell lung cancer, colon cancer, CNS cancer, melanoma, ovarian cancer, renal cancer, prostate cancer, breast cancer, thereby reproducibly demonstrating the high antitumor efficacy of the inventive compounds.

What is claimed is:

1. 3"-monohalocephalomannine of the formula:

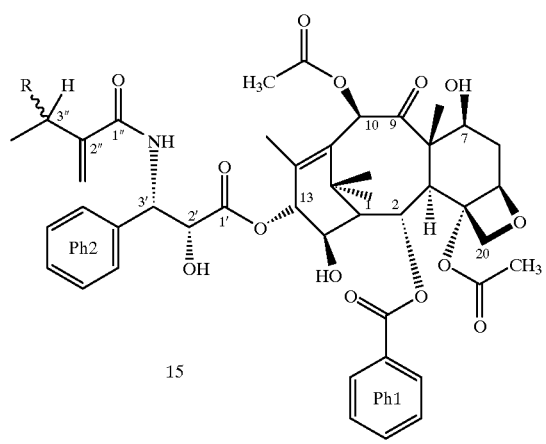

wherein R is halogen.

2. The compound of claim 1 wherein R is chlorine.
3. The compound of claim 1 wherein R is bromine.
4. The compound of claim 1 wherein R is a halogen selected from iodine and fluorine.
5. A pharmaceutical formulation which comprises as an active ingredient the compound of claims 1, 2, 3 or 4 or a pharmaceutically acceptable salt thereof.

6. A method for treating tumors in animals or humans which comprises administering to an animal or human in need thereof a tumor-sensitive amount of the compound of claims 1, 2, 3 or 4.

7. A method for the production of monohalocephalomannine comprising halogenating cephalomannine under conditions to selectively monohalogenate the side chain portion of cephalomannine to produce 3"-monohalocephalomannine.

8. The method of claim 7 wherein a compound selected from the group consisting of 3"-monochlorocephalomannine, 3"-monobromocephalomannine, 3"-monoiodocephalomonnme, or 3"-monofluorocephalomannine is produced.

9. The method of claims 7 or 8 wherein the cephalomannine is present in any amount in a mixture comprising paclitaxel and other taxane ring-containing compounds.

* * * * *